(12) United States Patent
McCombs et al.

(10) Patent No.: US 8,016,925 B2
(45) Date of Patent: Sep. 13, 2011

(54) MINI-PORTABLE OXYGEN CONCENTRATOR

(76) Inventors: Norman R. McCombs, Tonawanda, NY (US); Robert Bosinski, West Seneca, NY (US); Robert E. Casey, Tonawanda, NY (US); Michael R. Valvo, East Aurora, NY (US)

( * ) Notice: Subject to any disclaimer, the term of this patent is extended or adjusted under 35 U.S.C. 154(b) by 914 days.

(21) Appl. No.: 11/248,783

(22) Filed: Oct. 12, 2005

(65) Prior Publication Data

US 2006/0117957 A1 Jun. 8, 2006

Related U.S. Application Data (60) Provisional application No. 60/617,834, filed on Oct. 12, 2004.

(51) Int. Cl.
*B01D 53/02* (2006.01)
(52) U.S. Cl. .............. 96/121; 95/130; 96/109; 96/111; 96/130; 96/133; 96/144; 96/147; 128/205.11
(58) Field of Classification Search .................... 96/121, 96/111, 130, 109, 144, 133; 95/98, 130; 55/DIG. 35
See application file for complete search history.

(56) References Cited

U.S. PATENT DOCUMENTS

| | | | |
|---|---|---|---|
| 2,828,726 A * | 4/1958 | Kolbe ..................... 123/184.46 |
| 3,564,816 A | 2/1971 | Batta | |
| 3,636,679 A | 1/1972 | Batta | |
| 3,717,974 A | 2/1973 | Batta | |
| 4,302,224 A * | 11/1981 | McCombs et al. ............. 96/109 |
| 4,491,459 A | 1/1985 | Pinkerton | |
| 4,496,376 A * | 1/1985 | Hradek .......................... 96/112 |
| 4,512,781 A * | 4/1985 | Caralli et al. ...................... 95/98 |
| 4,648,888 A | 3/1987 | Rowland | |
| 4,802,899 A | 2/1989 | Vrana et al. | |
| 4,826,510 A * | 5/1989 | McCombs ..................... 96/127 |
| 4,925,464 A * | 5/1990 | Rabenau et al. ............... 96/124 |
| 4,971,609 A | 11/1990 | Pawlos | |
| 5,114,441 A * | 5/1992 | Kanner et al. ..................... 95/98 |
| 5,340,381 A * | 8/1994 | Vorih ................................ 95/21 |
| 5,531,807 A | 7/1996 | McCombs | |
| 5,549,736 A * | 8/1996 | Coffield et al. ................ 96/133 |
| 5,755,856 A | 5/1998 | Miyake et al. | |
| 5,827,358 A * | 10/1998 | Kulish et al. ................... 96/115 |
| 5,858,062 A | 1/1999 | McCulloh et al. | |

(Continued)

FOREIGN PATENT DOCUMENTS

JP 07-508205 9/1995

(Continued)

OTHER PUBLICATIONS

European Patent Office, Supplemental European Search Report, Mailed Dec. 15, 2009 and extended European Search Report dated Nov. 26, 2009.

*Primary Examiner* — Duane Smith
*Assistant Examiner* — Anthony Shumate
(74) *Attorney, Agent, or Firm* — Hiscock & Barclay, LLP (57) ABSTRACT

A compact and highly portable combination pressure swing adsorption apparatus and product gas conservation device for medical use, to produce efficiently a gas with a high concentration of oxygen and to deliver the oxygen concentrated gas to a user at selectable times and in selectable doses, in which the operating components are detachably mounted together as a single unit.

20 Claims, 13 Drawing Sheets

U.S. PATENT DOCUMENTS

| | | | |
|---|---|---|---|
| 5,871,564 A | 2/1999 | McCombs | |
| 6,036,754 A * | 3/2000 | Rowe | 96/130 |
| 6,427,690 B1 | 8/2002 | McCombs et al. | |
| 6,478,850 B1 | 11/2002 | Warren | |
| 6,520,176 B1 | 2/2003 | Dubois et al. | |
| 6,524,370 B2 | 2/2003 | Maheshwary et al. | |
| 6,547,851 B2 | 4/2003 | Warren | |
| 6,764,534 B2 | 7/2004 | McCombs et al. | |
| 6,953,498 B2 * | 10/2005 | Walker et al. | 96/130 |
| 7,273,051 B2 * | 9/2007 | Whitley et al. | 128/205.11 |
| 2002/0096174 A1 | 7/2002 | Hill et al. | |
| 2002/0121191 A1 * | 9/2002 | Warren | 95/11 |
| 2003/0005928 A1 | 1/2003 | Appel et al. | |
| 2003/0167924 A1 * | 9/2003 | McCombs et al. | 96/121 |
| 2005/0005771 A1 * | 1/2005 | Lomax et al. | 96/121 |
| 2008/0047435 A1 * | 2/2008 | Dolensky et al. | 96/116 |

FOREIGN PATENT DOCUMENTS

| | | |
|---|---|---|
| JP | 09-24098 | 1/1997 |
| JP | 2002-504022 | 2/2002 |
| JP | 2002-241110 A2 | 8/2002 |
| WO | WO 9316786 A1 * | 9/1993 |
| WO | WO 9857728 A1 * | 12/1998 |
| WO | WO 03/090903 A | 11/2003 |

* cited by examiner

MINI-PORTABLE OXYGEN CONCENTRATOR

CROSS-REFERENCE TO RELATED APPLICATIONS

This application claims priority from U.S. Provisional Patent Application Ser. No. 60/617,834, filed Oct. 12, 2004.

FIELD OF THE INVENTION

This invention relates generally to gas concentration apparatus for separating gas mixtures by pressure swing adsorption ("PSA") and vacuum pressure swing adsorption ("VPSA"), and more particularly to PSA and VPSA apparatus intended to deliver oxygen for medical use.

BACKGROUND OF THE INVENTION

The general type and operating principles of PSA and VPSA, which are well known, are described, for example, in U.S. Pat. Nos. 3,564,816; 3,636,679; 3,717,974; 4,802,899; 5,531,807; 5,755,856; 5,871,564; 6,524,370; and 6,764,534, among others. Both PSA and VPSA apparatus may include one or more adsorbers, each having a fixed sieve bed of adsorbent material to fractionate at least one constituent gas from a gaseous mixture by adsorption into the bed, when the gaseous mixture from a feed stream is sequentially directed through the adsorbers in a co-current direction. While one adsorber performs adsorption, another adsorber is simultaneously purged of its adsorbed constituent gas. In a PSA apparatus, the purging is performed by part of the product gas being withdrawn from the first or producing adsorber and directed through the other adsorber in a counter-current direction. In a VPSA apparatus, the purging primarily is performed by a vacuum produced at the adsorber inlet to draw the purged gas from the adsorber. Once the other adsorber is purged, the feed stream at a preset time is then directed to the other adsorber in the co-current direction, so that the other adsorber performs adsorption. The first adsorber then is purged either simultaneously, or in another timed sequence if there are more than two adsorbers, all of which will be understood from a reading of the above described patents.

When, for example, such apparatus is used to produce a high concentration of oxygen from ambient air for use in various applications, whether medical, industrial or commercial, air which enters the apparatus typically contains about 78% nitrogen, 21% oxygen, 0.9% argon, and a variable amount of water vapor. Principally, most of the nitrogen is removed by the apparatus to produce a gas product, which for medical purposes, for example, typically may contain at least about 80% oxygen. Most such apparatus for medical uses generally are too bulky for use by patients who are traveling or otherwise wish to leave their home environments for any purpose. In those cases, patients will normally forego the use of oxygen concentrators and revert to the use of pressurized oxygen tanks. While oxygen tanks have been very useful in enabling patients to be more ambulatory, they nevertheless are restricted in use, as for example because of limited oxygen storage capacity or because their use may be prohibited in certain modes of public. transportation or locations where flammable materials can create a hazard. Although the useful life of oxygen tanks may be extended by the use of oxygen concentration devices ("OCD"), as disclosed, for example, in co-owned U.S. Pat. No. 6,427,690, McCombs et al., issued Aug. 6, 2002, their use nevertheless continues to be problematic because of safety and storage concerns, access to resupplies of oxygen, and continuing medical expenses and reimbursement paperwork for the oxygen.

There having been developed a particularly useful and highly portable oxygen concentrator used for medical purposes and operating on PSA principles as disclosed in co-owned U.S. Pat. No. 6,764,534, McCombs et al., issued Jul. 20, 2004, the entire disclosure of which is incorporated by reference, the present invention builds on that knowledge by an even more compact, lighter weight and very highly portable oxygen concentrator for medical uses.

As is now well known, the most effective use of inhaled oxygen occurs at the onset of inhalation, and various devices have been constructed to deliver oxygen from pressurized oxygen tanks only when inhalation is first sensed by the devices and only during the initial stage of the inhalation cycle. U.S. Pat. No. 6,764,534, for example, discloses a system that primarily only delivers oxygen at the initial stage of inhalation by detecting a drop in pressure as sensed by inhalation of a user through a conventional cannula (not shown) to actuate a transducer circuitry causing a flow control valve to be opened for a predetermined time and allow a predetermined amount of the oxygen enriched gas to be delivered to the user in oxygen concentrations up to about 95%.

SUMMARY OF THE INVENTION

The present invention provides an oxygen concentrator apparatus that can operate by either PSA or VPSA principles, attain the required concentrations of oxygen for the desired application(s), yet be highly portable and easily manipulated and transported even by patients with relatively limited physical capacities. This is accomplished by a unique configuration of operating components combined in an inventive structural design.

The intended use of the apparatus is to deliver supplemental, high-purity oxygen to persons who suffer, for example, from various forms of chronic obstructive pulmonary disease (COPD). The invention preferably uses a two-bed concentrator together with an integrated OCD or flow controller to provide oxygen in predetermined doses up to an equivalent of about 3 liters per minute (LPM) effective rate of a continuous product gas with a high oxygen concentration at over 90%, and with an overall weight of only about 5 pounds.

BRIEF DESCRIPTION OF THE DRAWING

The foregoing and other objects, features and advantages of the invention will become more apparent from a reading of the following description in connection with the accompanying drawing of a preferred embodiment of the invention, in which.

DETAILED DESCRIPTION OF THE PREFERRED EMBODIMENT

Turning now to the drawings and in accordance with the present invention, there is shown a preferred embodiment, generally indicated as 20, of a combined oxygen concentrator and oxygen conserving device 20 used for fractionating at least one component, namely nitrogen, from a gaseous mixture, generally but not necessarily ambient air, by pressure swing adsorption to produce a product gas, and for delivering the product gas at specific and variable intervals upon demand by a user.

Figure 1:
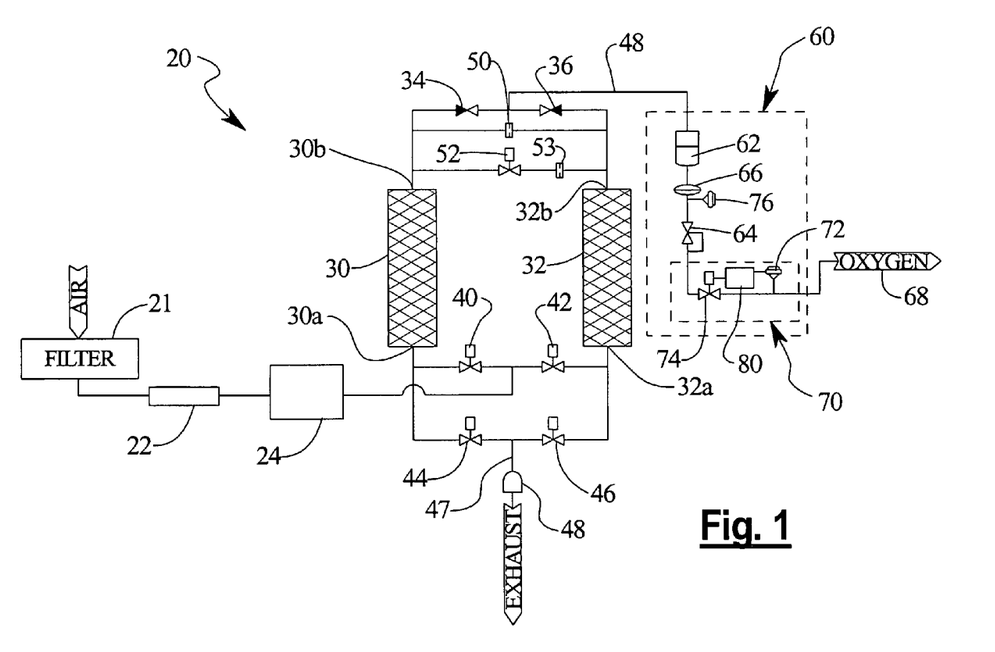
FIG. 1 is a schematic illustration of a combined PSA/OCD apparatus according to the invention.

With reference to FIG. 1, ambient air is supplied to a PSA/OCD apparatus 20 through a filtered intake 21 and an intake resonator 22 to decrease the noise from the intake of the ambient air feed stream. The feed stream continues from resonator 22 and is moved by a feed air compressor/heat exchanger assembly 24 alternatively to first and second adsorbers 30, 32 through feed valves 40 and 42 respectively.

When the feed stream alternatively enters inlets 30a, 32a of adsorbers 30, 32 in a co-current direction, the respective adsorber fractionates the feed stream into the desired concentration of product gas. The adsorbent material used for the beds to separate nitrogen from the ambient air may be a synthetic zeolite or other known adsorber material having equivalent properties.

The substantial or usable portion of the oxygen enriched product gas generated by the ambient air flowing in the co-current direction sequentially in each one of the adsorbers 30, 32 is directed through the outlet 30b, 32b and check valve 34, 36 of the corresponding adsorber to a product manifold 48 and then to a delivery control assembly 60, as will be described. The balance of the product gas generated by each adsorber is timed to be diverted through a purge orifice 50 and a properly timed equalization valve 52 and an optional flow restrictor 53 to flow through the other adsorber 30 or 32 in the counter-current direction from the respective outlet 30b, 32b and to the respective inlet 30a, 32a of the other adsorber to purge the adsorbed, primarily nitrogen, gases. The counter-current product gas and purged gases then are discharged to the atmosphere from the adsorbers through properly timed waste valves 44, 46, common waste line 47 and a sound absorbing muffler 48.

Control assembly 60, to which the usable portion of the product gas directed according to the invention, includes a mixing tank 62 which also may be filled with synthetic zeolite and serves as a reservoir to store product oxygen before delivery to the user through an apparatus outlet 68 in the pulse dose mode, a piston-type pressure control regulator 64 to regulate the product gas pressure to be delivered to the user, a bacteria filter 66, and an oxygen delivery system 70 including a pulse dose transducer 72 including the flow controller 80 to be described, a flow control solenoid operated valve 74, and a low pressure sensor 72. Delivery of the PSA generated oxygen concentrated gas from the mixing tank 62 to the user is controlled by the delivery system 70 as will be described.

Figure 2:
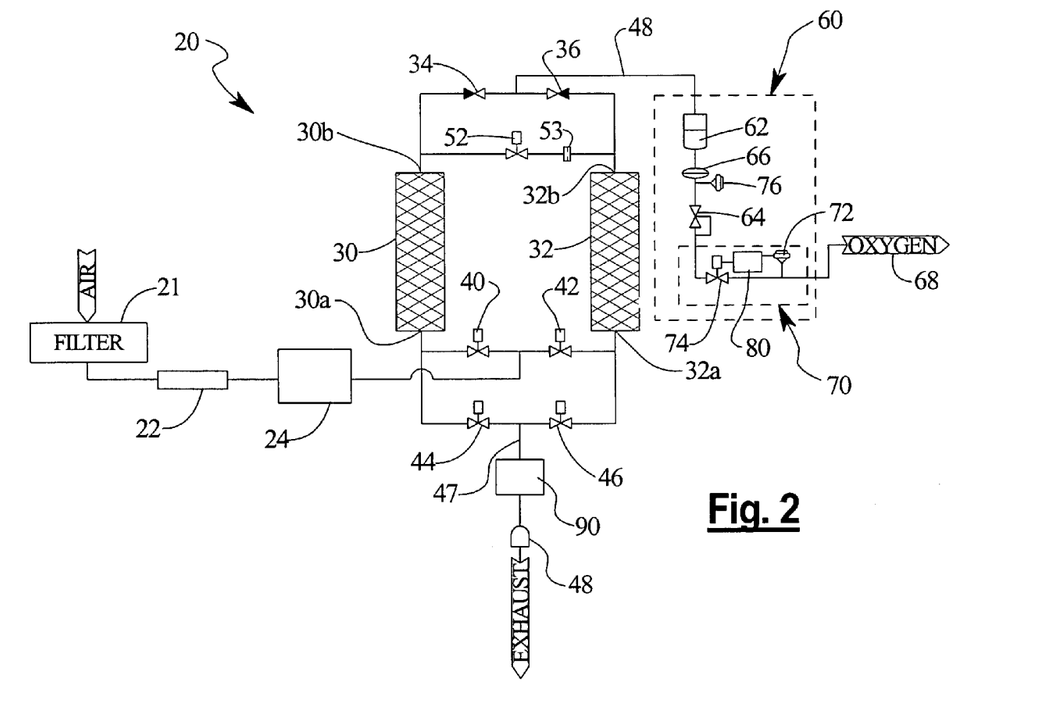
FIG. 2 is a schematic illustration of a combined VPSA/OCD apparatus according to the invention.

A VPSA/OCD apparatus as schematically shown in FIG. 2 operates in similar fashion as the PSA apparatus of FIG. 1, except that purge orifice 50 may be eliminated. In its stead, a vacuum pump 90 is provided in the common waste line 47 to draw the waste nitrogen alternately from each of adsorber beds 30 32 upon the timed opening of the respective waste valve 44, 46. The cycling of ambient air and operation of the feed and waste valves to produce the oxygen enriched product gas, as well as of supply of product gas to mixing tank 62 and the delivery of the product gas by flow controller 80, otherwise are as described with respect to FIG. 1.

Figure 4:
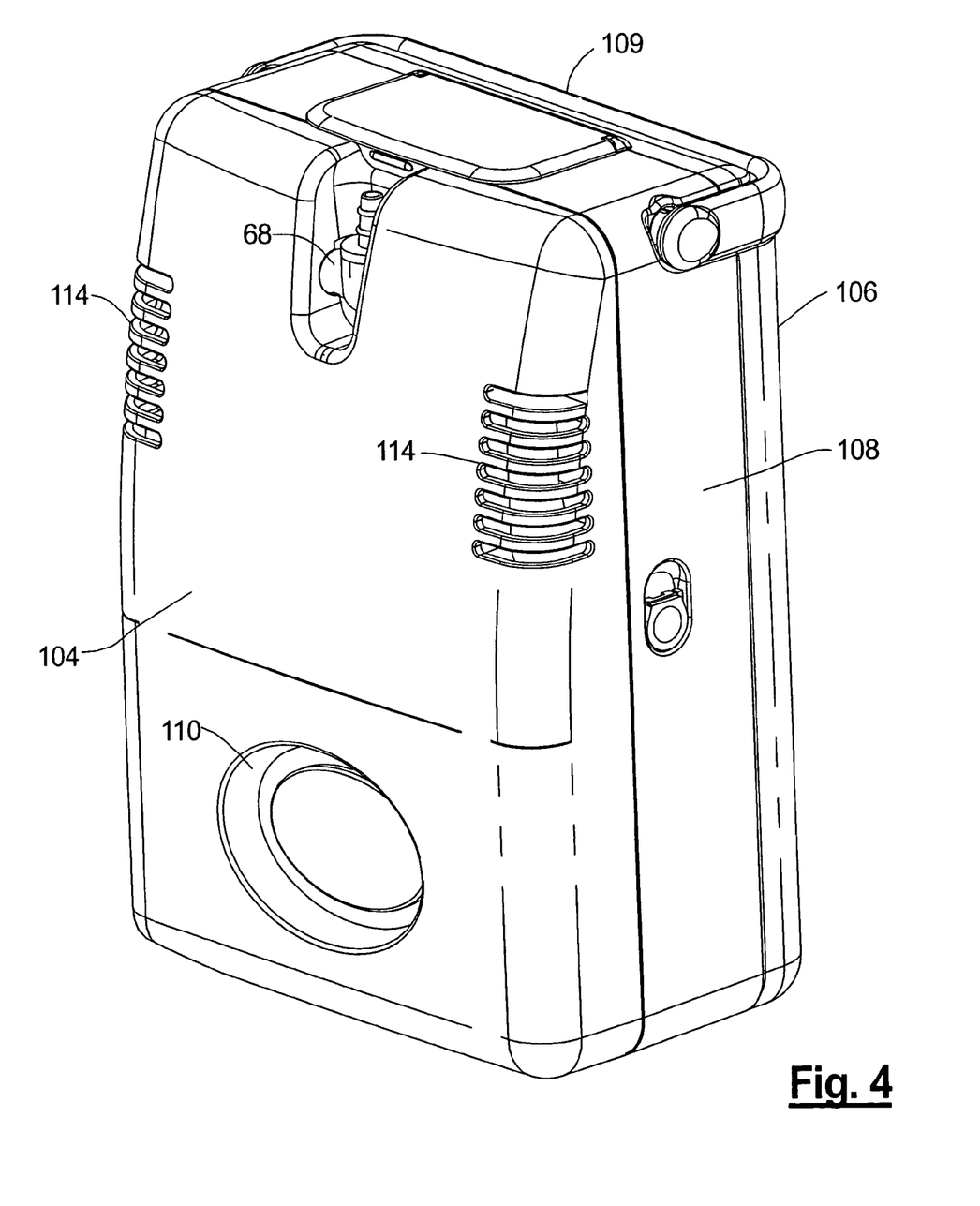
FIGS. 4, 5 and 6 are a perspective view, a top view and a bottom view of an assembled preferred embodiment of the invention.
Figure 5:
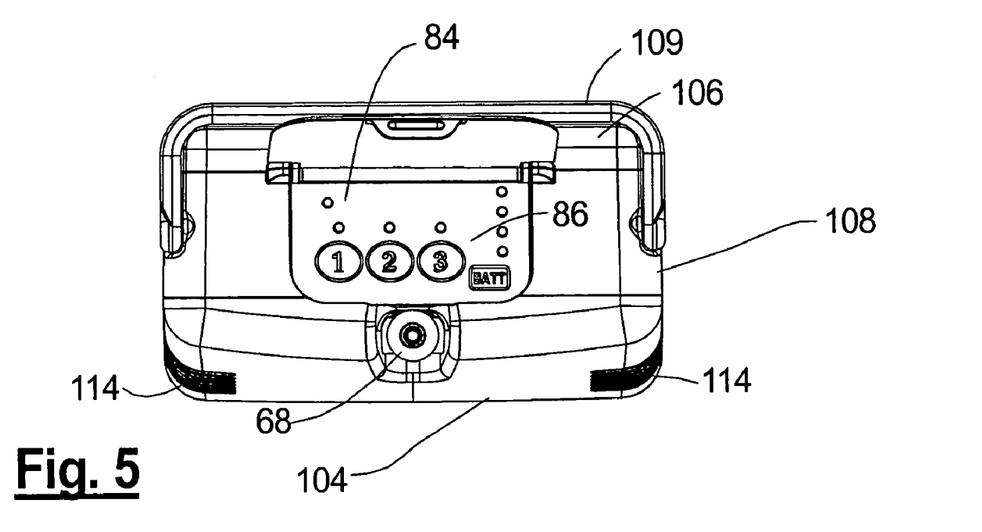
Figure 6:
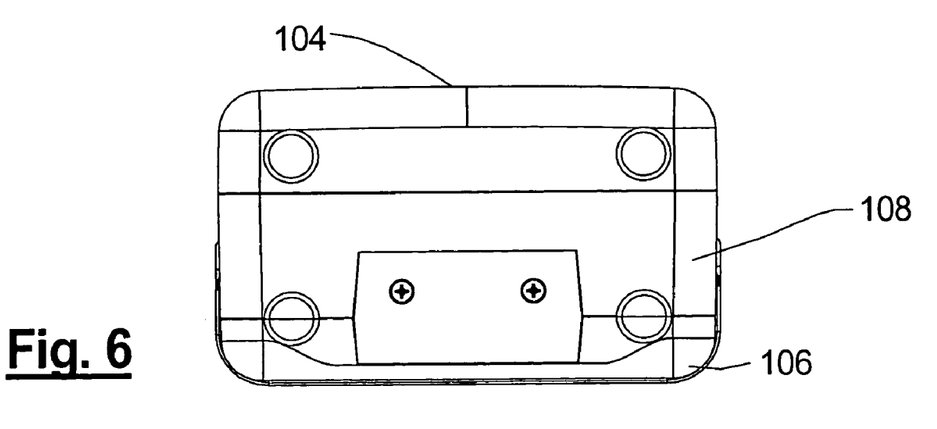

As shown in FIGS. 4 through 6, apparatus 20 according to a preferred embodiment of the invention includes a front housing enclosure 104, a rear housing enclosure 106, and a central chassis 108 on which are mounted the majority of the operating components of the apparatus 20. The outer housing portions 104, 106 and chassis 108 may be of any suitable impact resistant material, but preferably is an injection molded ABS plastic. Chassis 108 as shown also includes a pivotable carry handle 109.

Within front enclosure 104 is an access vent 110 by which ambient air in drawn through an air filter 112 by an internal fan 92 into the interior of apparatus 20, and two side exhaust vents 114 by which cooling air circulating through the interior and waste gases from beds 30,32 are exhausted from apparatus 20.

The effectiveness and highly compact size and light weight of the invention is made possible in large part because of a novel manifold structure and interconnection of the components of the invention as will now be described.

According to the invention, operating components of unique design are all assembled in an integrated configuration as illustrated in FIGS. 7 through 13b. As shown, adsorber beds 30, 32 are mounted vertically between and in fluid communication with both feed/waste manifold 120 and a product manifold 122. Mounted to the sides of beds 30, 32 on feed/waste manifold 120 are feed valves 40, 42 and waste valves 44, 46, respectively. Below the valves and to provide fluid communication with both heads of double headed compressor 24 (to be described) are access fittings 124, 126 fixed to feed/waste manifold 120 and connecting the outlets of compressor 24 to deliver the ambient air from compressor 24 to manifold 120, where it is directed by internal channels to the respective feed valves 40, 42 to be alternately fed through manifold 120 to beds 30, 32. In the VPSA embodiment of the invention, one of the compressor heads is configured to provide vacuum to remove the waste gases from both heads. In this embodiment, manifold 120 is configured to provide fluid connection from only the pressure side of compressor 24 to both beds through the feed valves 40, 42, whereas manifold 120 has a separate fluid connection to the vacuum side of compressor 24. through the waste valves 44, 46 to both heads.

Figure 7:
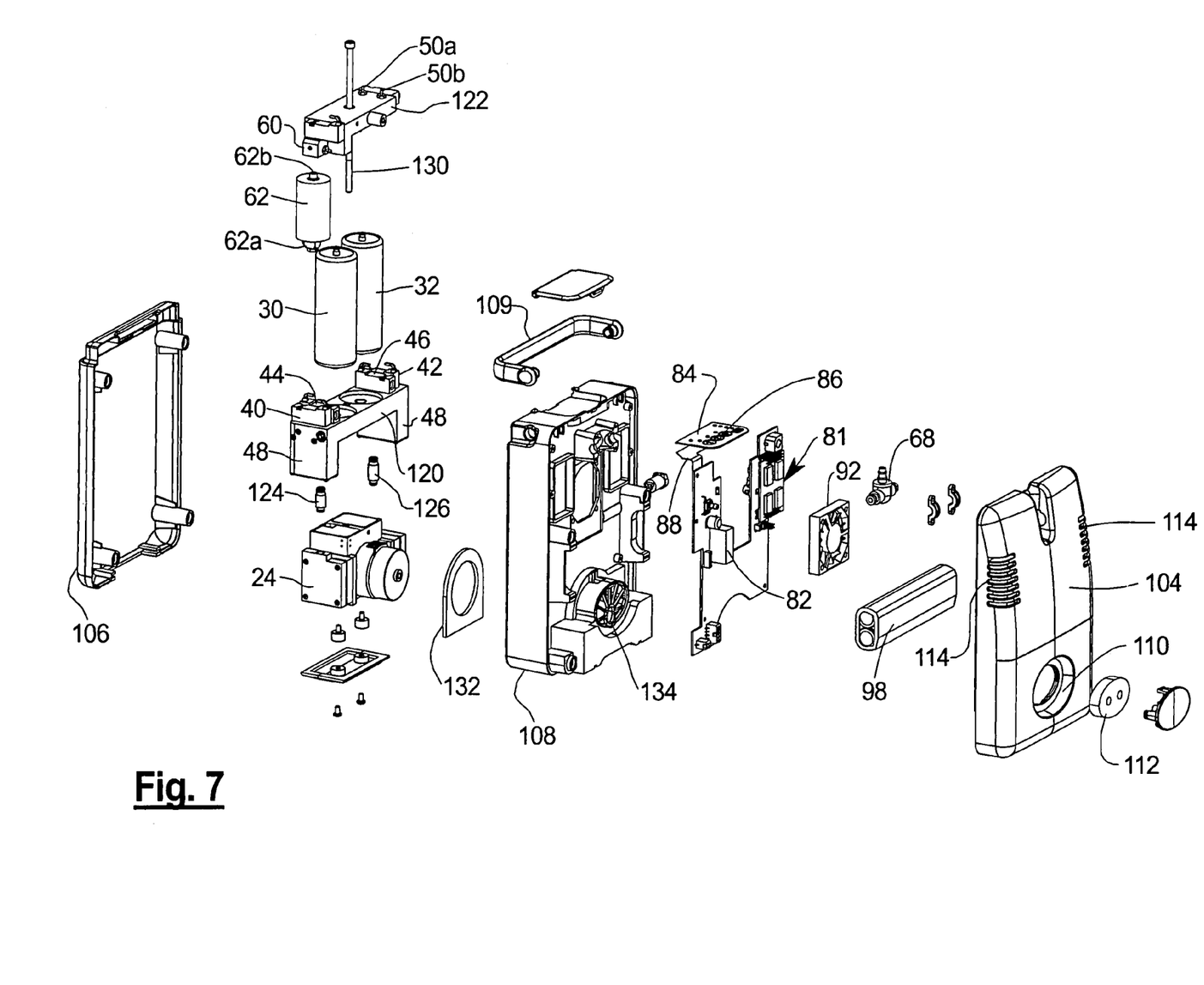
FIG. 7 is an exploded view of the preferred embodiment.
Figure 8:
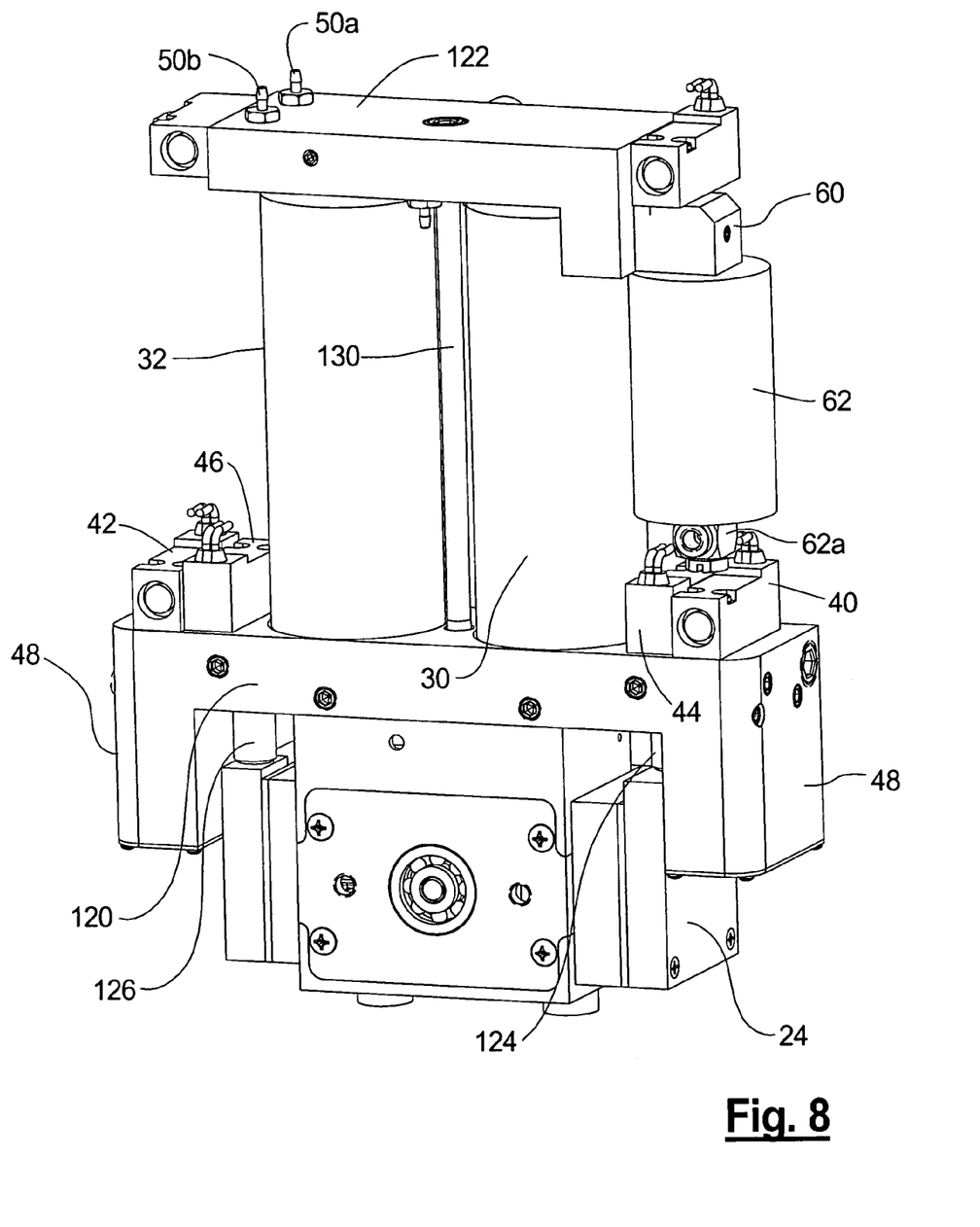
FIG. 8 is an assembled view of the operating components of the preferred embodiment.
Figure 9:
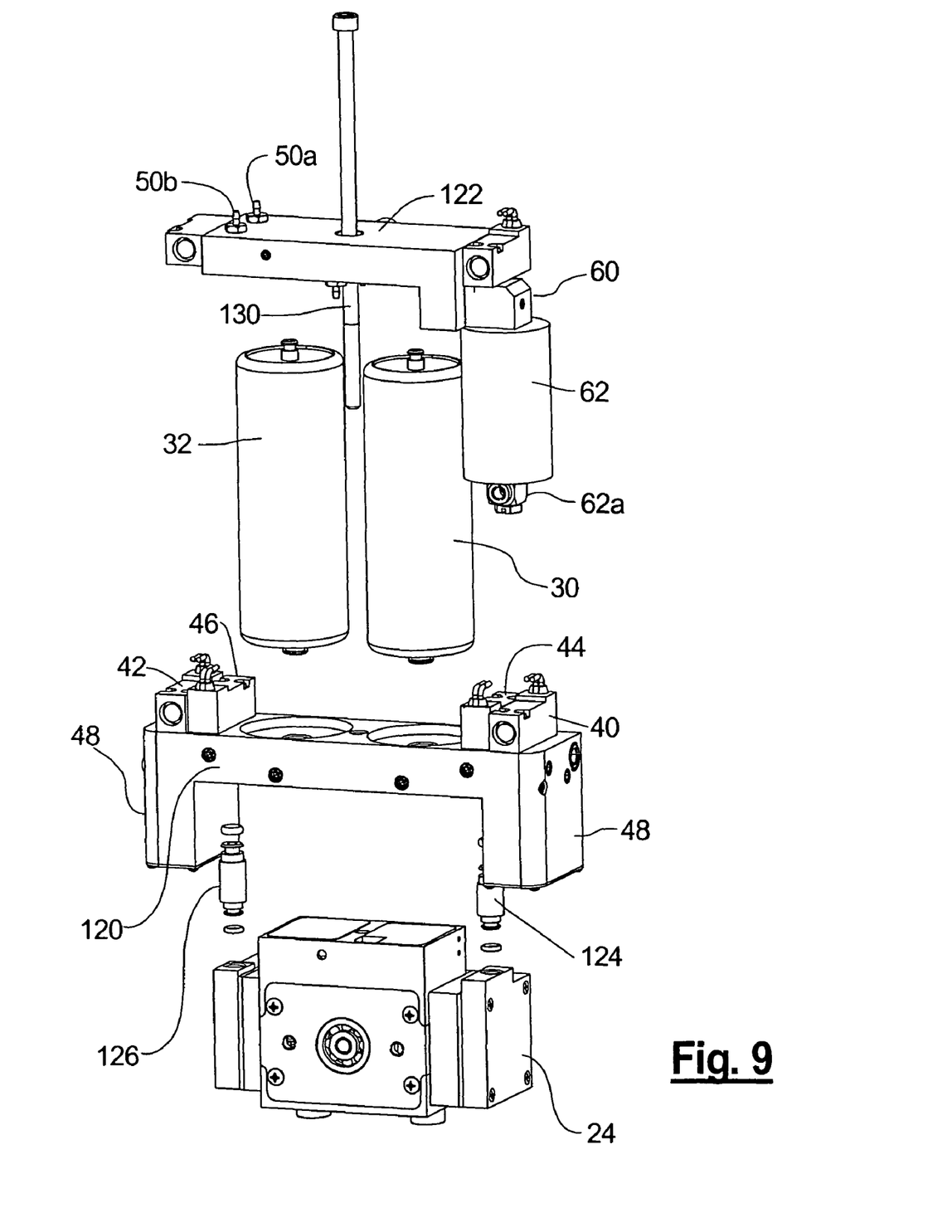
FIG. 9 is an exploded view of the operating components of the preferred embodiment.
Figure 10A:
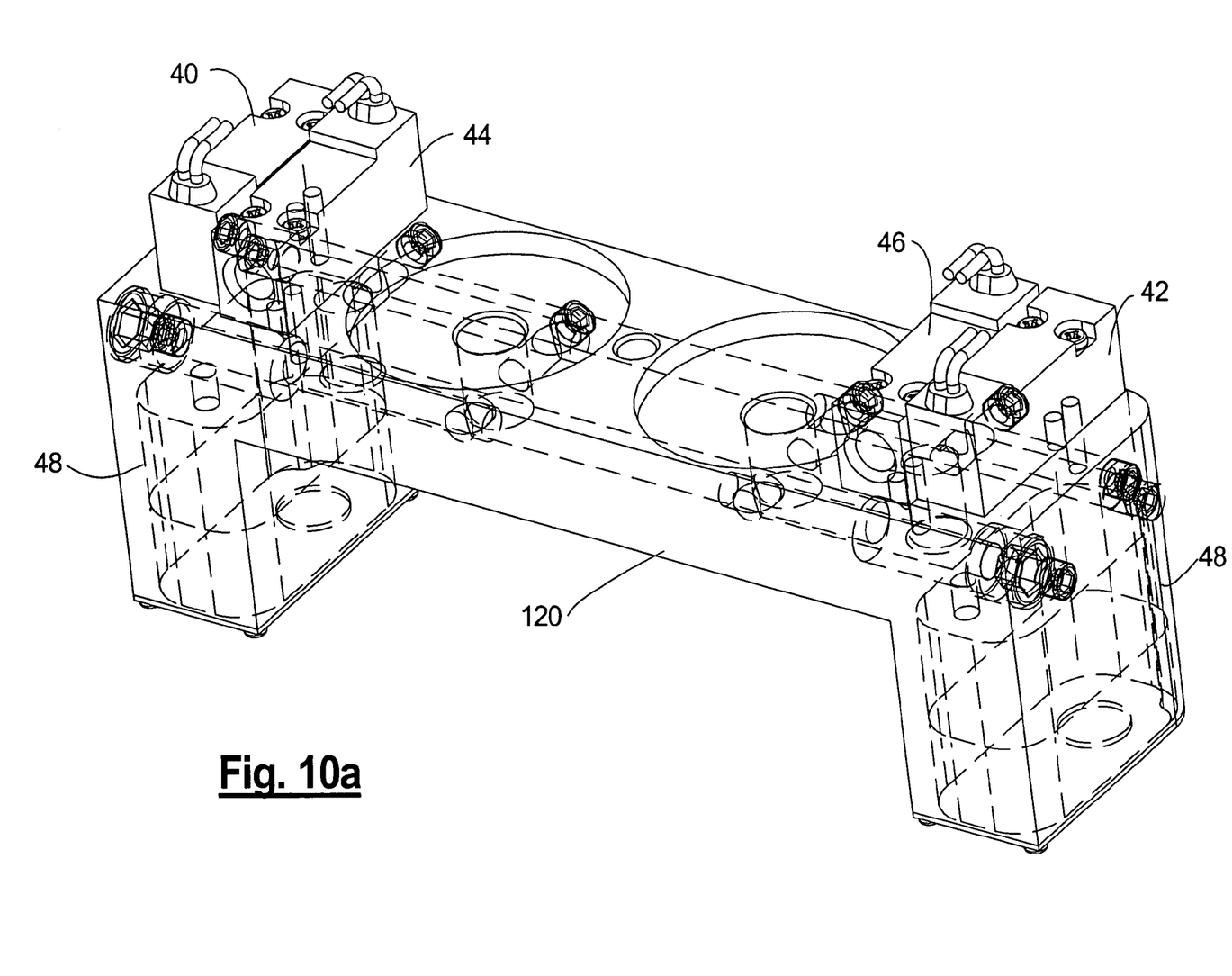
FIGS. 10a-10f and 11a-11d are isometric and cross-sectional views of the feed/waste manifold and of the product manifold, respectively, of the preferred embodiment.
Figure 10B:
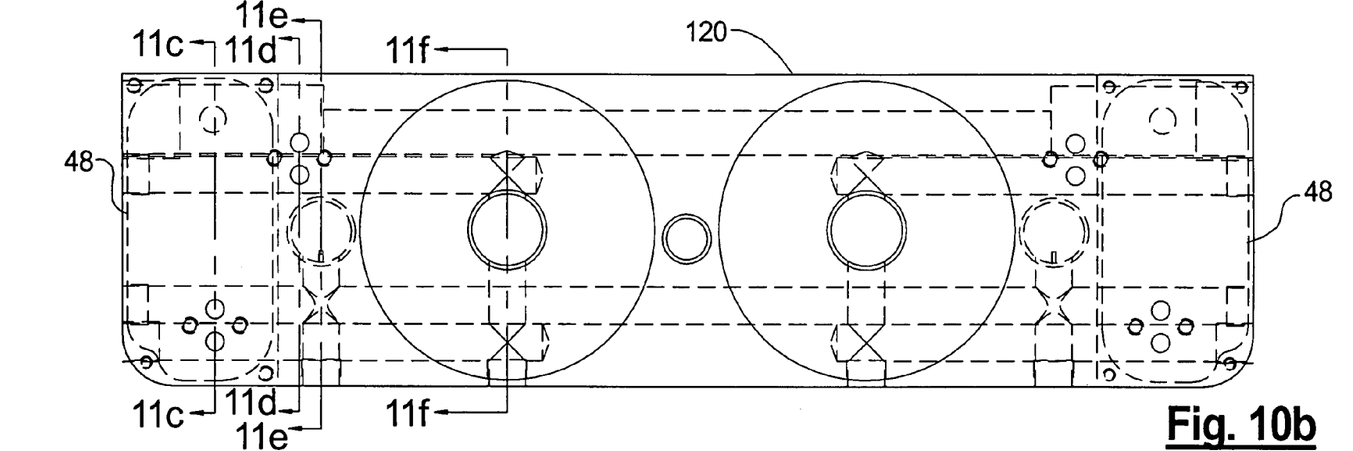
Figure 10C:
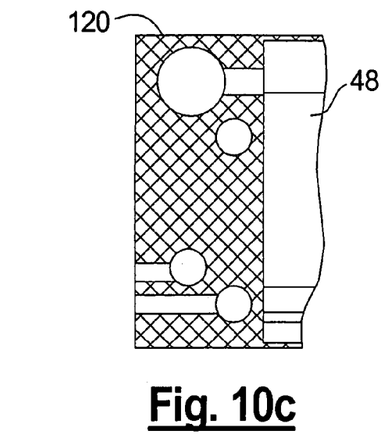
Figure 10D:
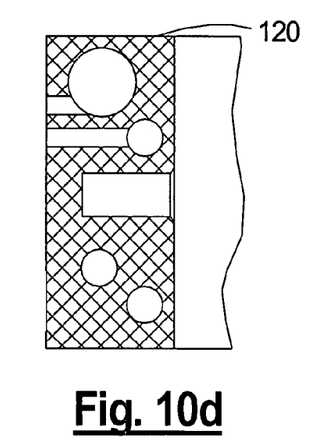
Figure 10E:
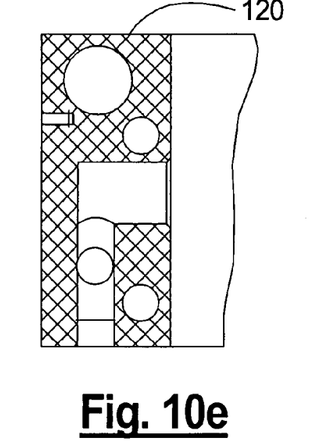
Figure 10F:
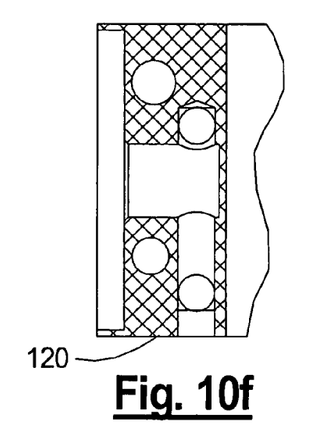
Figure 11A:
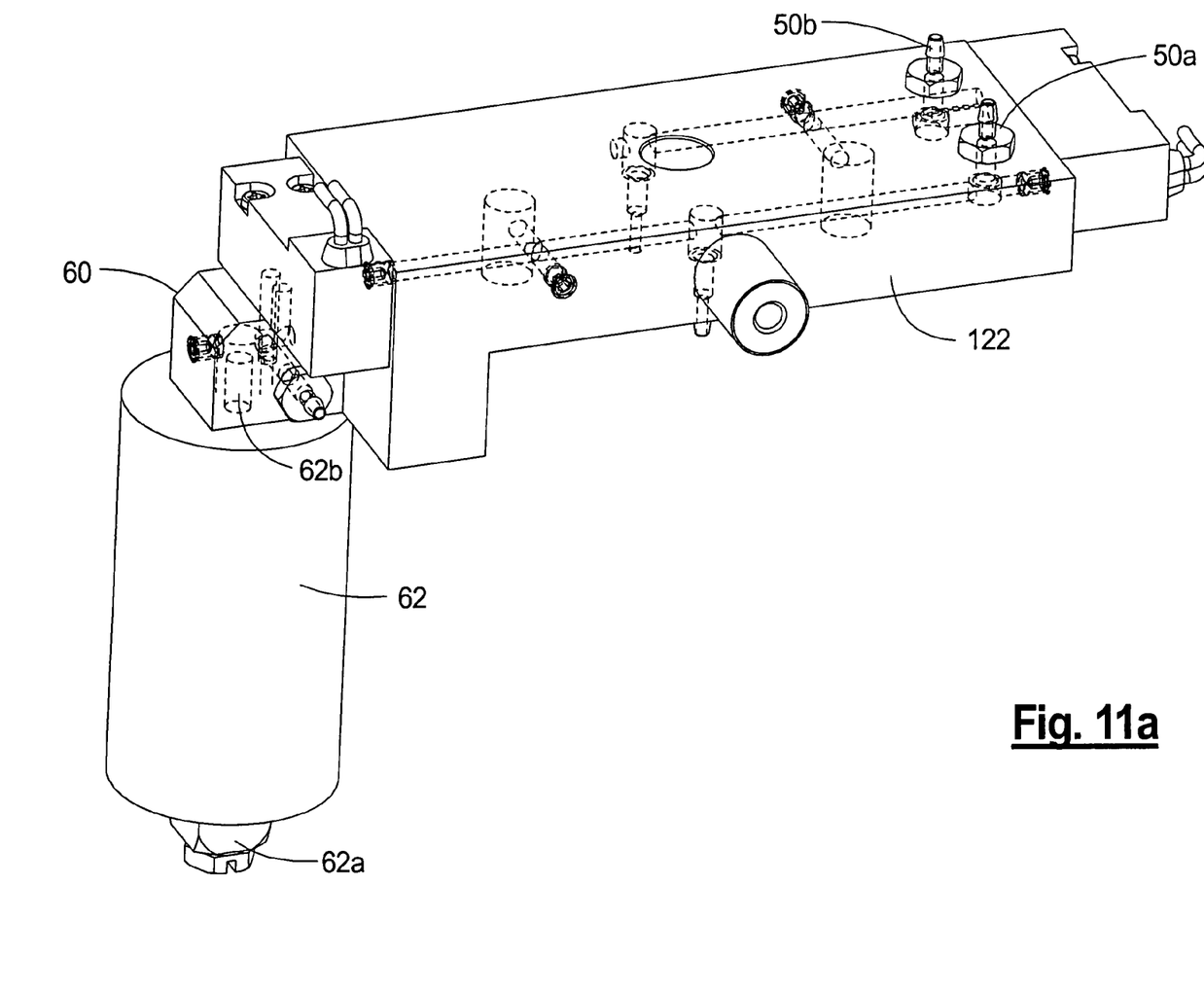
Figure 11B:
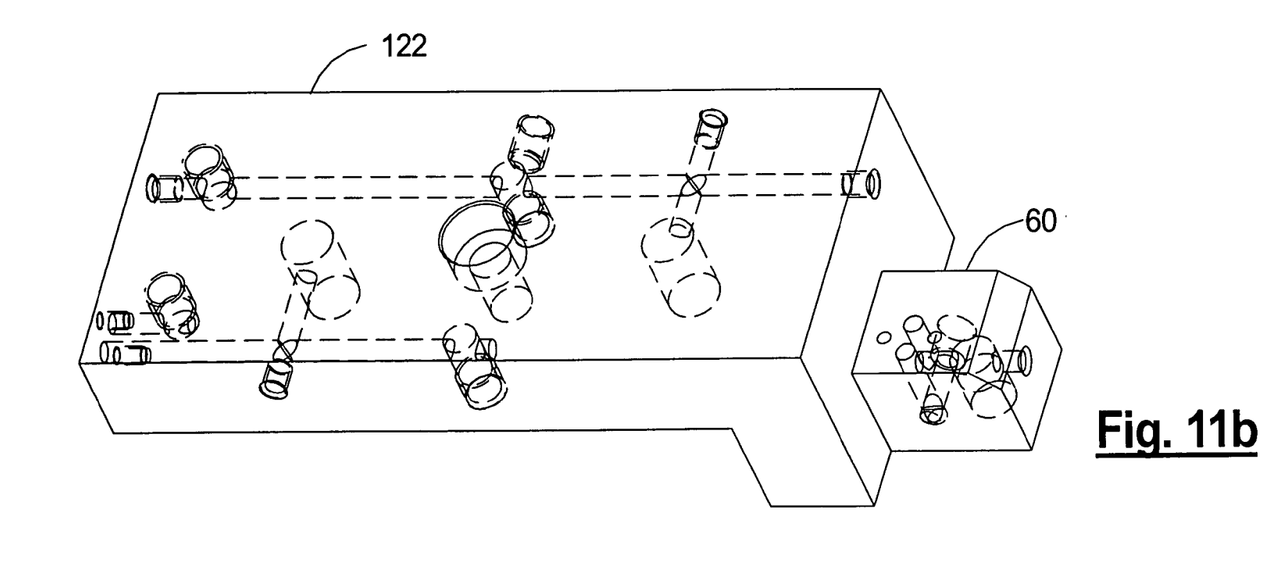
Figure 11C:
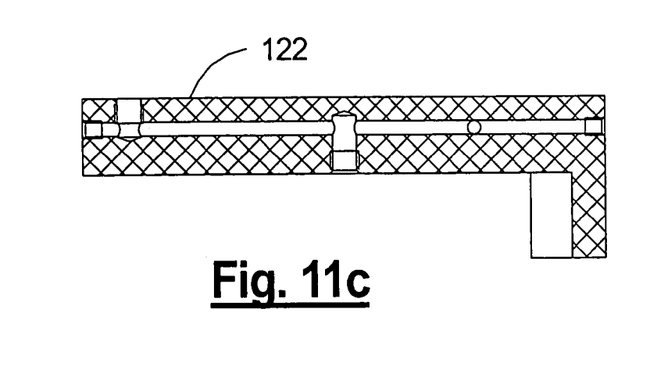
Figure 11D:
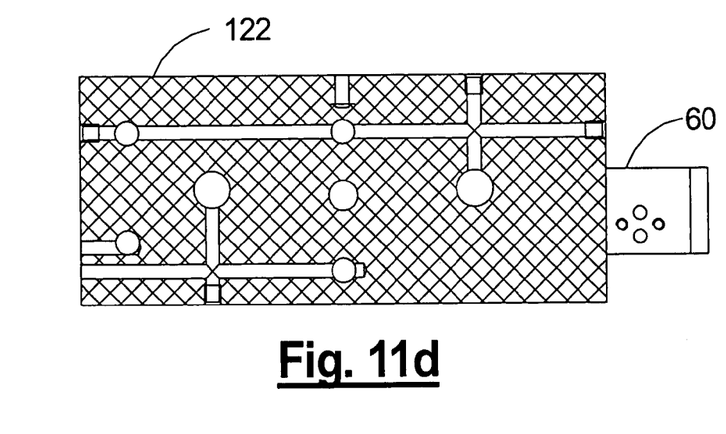

Product gas is delivered from beds 30, 32 by fluid connection of bed outlets 30b, 32b to product manifold 122, in which channels are cut to deliver product gas through fitting 122a and by tubing (not shown) to the inlet side 62a of mixing tank 62. In the PSA embodiment of apparatus 20, a portion of the product gas is redirected by purge orifice 50 connected between fittings 50a and 50b and equalization valve 52 to the idle adsorber bed, whereas in the VPSA embodiment, the purge orifice is eliminated and virtually all of the product gas is delivered to mixing tank 62. Mixing tank 62 is mounted on product manifold 122 at its outlet side 62b, where it is in fluid connection through manifold 122 with delivery control assembly 60 also affixed to manifold 122 as shown.

The two beds 30, 32, the two manifolds 120, 122 and compressor 24 are then held together as a compact unit, as shown, by a single elongated bolt 130 passing through manifolds 120, 122, between beds 30, 32 and threaded to compressor 24. The unit as assembled is then attached to central chassis 108 by suitable shock absorbing means. As thus constructed, it is apparent that the mechanical components of apparatus 20 can now be readily assembled in production and readily accessed for servicing.

Figure 12:
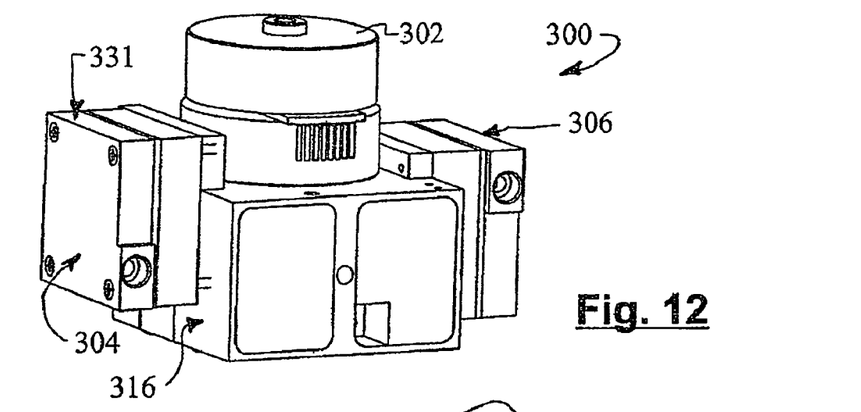
FIGS. 12, 13a, and 13b are views of the compressor as used in the preferred embodiment.
Figure 13A:
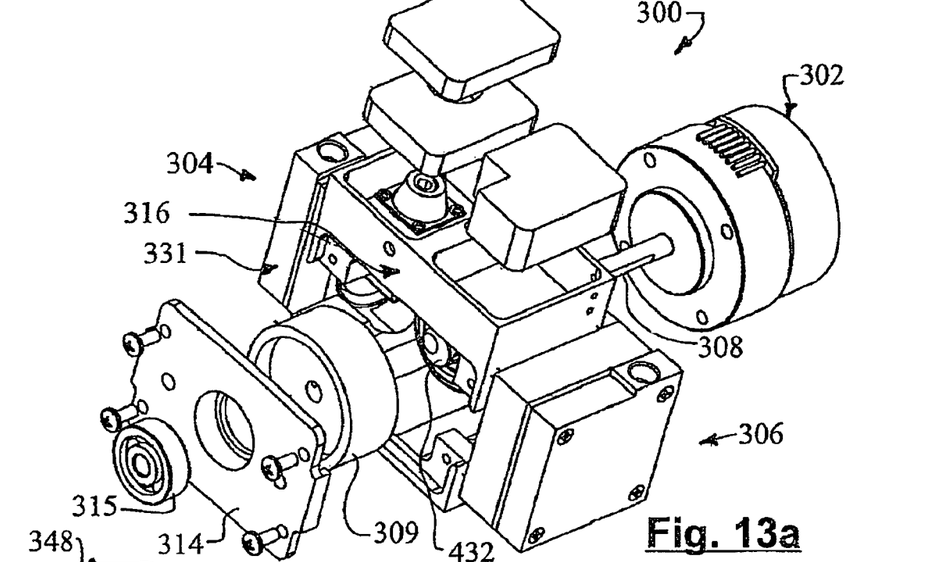
Figure 13B:
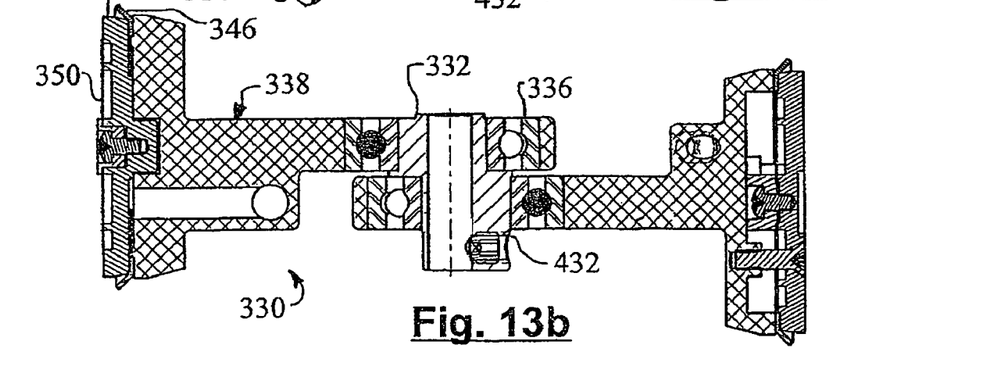

With reference to FIGS. 12, 13*a*, and 13*b*, a preferred compressor as used in the invention is the compact compressor 300 disclosed as a second embodiment of the invention disclosed in co-owned and co-pending U.S. non-provisional patent application Ser. No. 10/932,183, filed Sep. 1, 2004, the entire disclosure of which is incorporated by reference herein. For the apparatus operating in the PSA mode, the compressor includes a single-shaft motor 302, a central housing 316, and two opposing pressure heads 304, 306. However, for operation in the VPSA mode, one head, e.g., 304 comprises the pressure-side compressor head, and head 306 the vacuum-side compressor head.

The motor 302 is a standard electric motor is securely mounted to the central housing 316 with the drive shaft 308 penetrating the central housing 316. Central housing 316 is configured to support both compressor heads 304, 306, each of which as disclosed in the above identified non-provisional application includes an inlet chamber with an inlet filter, an outlet chamber with an outlet filter, a counterweight 309, a drive shaft support plate 314, and a drive shaft support bearing 315. Depending on the function and the gases to be moved, one of the compressor heads 304, 306 may have a longer stroke and therefore have a larger eccentric core. The counterweight 309 is configured to even out the weight distribution on the drive shaft 308 to thereby reduce vibration of the drive shaft 308. The drive shaft support plate 314 closes the central housing 316 and supports the drive shaft support bearing 315, which supports the free end of the drive shaft 308.

In the VPSA mode in which one compressor head supplies pressure and the other compressor head supplies a vacuum, the pressure-side compressor head 304 includes a pressure-side piston assembly 330 and a pressure-side chamber assembly 331. The pressure-side piston assembly 330 includes a pressure-side eccentric core 332, a bearing 336, a pressure-side piston 338, a piston seal 346, a pressure-side retaining plate 348, and a pressure-side intake flapper 350. The vacuum-side compressor head 306 includes a vacuum-side piston assembly and a vacuum-side chamber assembly. In this case, the vacuum-side eccentric core may have a different radius than the pressure-side eccentric core such that the vacuum-side piston assembly has a longer or shorter stroke than the pressure-side piston assembly 330. Further, the vacuum-side eccentric core 432 may have a different phase than the pressure-side eccentric core 332. For example, the vacuum-side eccentric core may be phased about 180° from the pressure-side eccentric core such that the vacuum-side piston assembly is at the top dead center position when the pressure-side piston assembly is also at the top dead center position.

Further details of the compressor and its operation in either or both PSA and VPSA modes will be clear from a reading of the co-pending non-provisional application.

In operation, ambient air is caused by fan 92 to enter the enclosed interior of apparatus 20 through inlet 110 on the front cover 104 and supporting a filter 112 of a gross-particulate foam, designed to remove dust and other impurities, from the air entering the apparatus interior. A portion of the ambient air which enters the interior of apparatus 20 is caused by the compressor 24 to flow into resonator 22 through a second filter made of felt material at intake 21 to further filter the air to be fractionated. The balance of the ambient air flowing into the interior of the apparatus 20 is caused by fan 92, baffle 132, and static flow directing vanes 134 to flow in a controlled path throughout the enclosed interior of the apparatus to cool the operating elements of apparatus 20 before exiting side exhaust vents 114.

A combined PSA/OCD based on the preferred embodiment is easily able to deliver an oxygen concentration, at standard atmosphere in excess of about 90% in pulse doses at every inhalation cycle of about 8.75 mL for the setting of 1 LPM, about 17.5 mL for the setting of 2 LPM, and about 26.25 mL for the setting of 3 LPM. Quite surprisingly, this performance can be achieved in an apparatus with a weight of less than about 5 lb., measuring overall less than 4" (or about 3.6") in depth, less than 7" (or about 6.6") in width and less than 9" (or about 8.6") in height, and emitting less than about 55 decibels in noise level.

In the embodiments shown, each of the adsorber beds 30, 32 for a medical application may have about a half liter capacity and be about 5.25 inches in length and about 1.375 inches in diameter, with the zeolite sieve material weighing about 50 grams for each adsorber bed. Preferably, the beds 30, 32 are spring biased in order not to "fluidize" the sieve material in their depressurization or pressure equalization stages. The feed stream of air is provided at a nominal rate of about 6 LPM, to produce a product gas within an approximate operating system pressure range from about 27.7 psia to about 39.7 psia, with the setting at 3 LPM and a user breathing rate of about fifteen breaths per minute.

The circuit components on a printed circuit board 81 control the PSA cycle and the pulse dosing of oxygen from the apparatus. A flexible wiring strip 88 connects the accessible operating switches 86 and indicators on control panel 84 to the circuit board 81.

Figure 3:
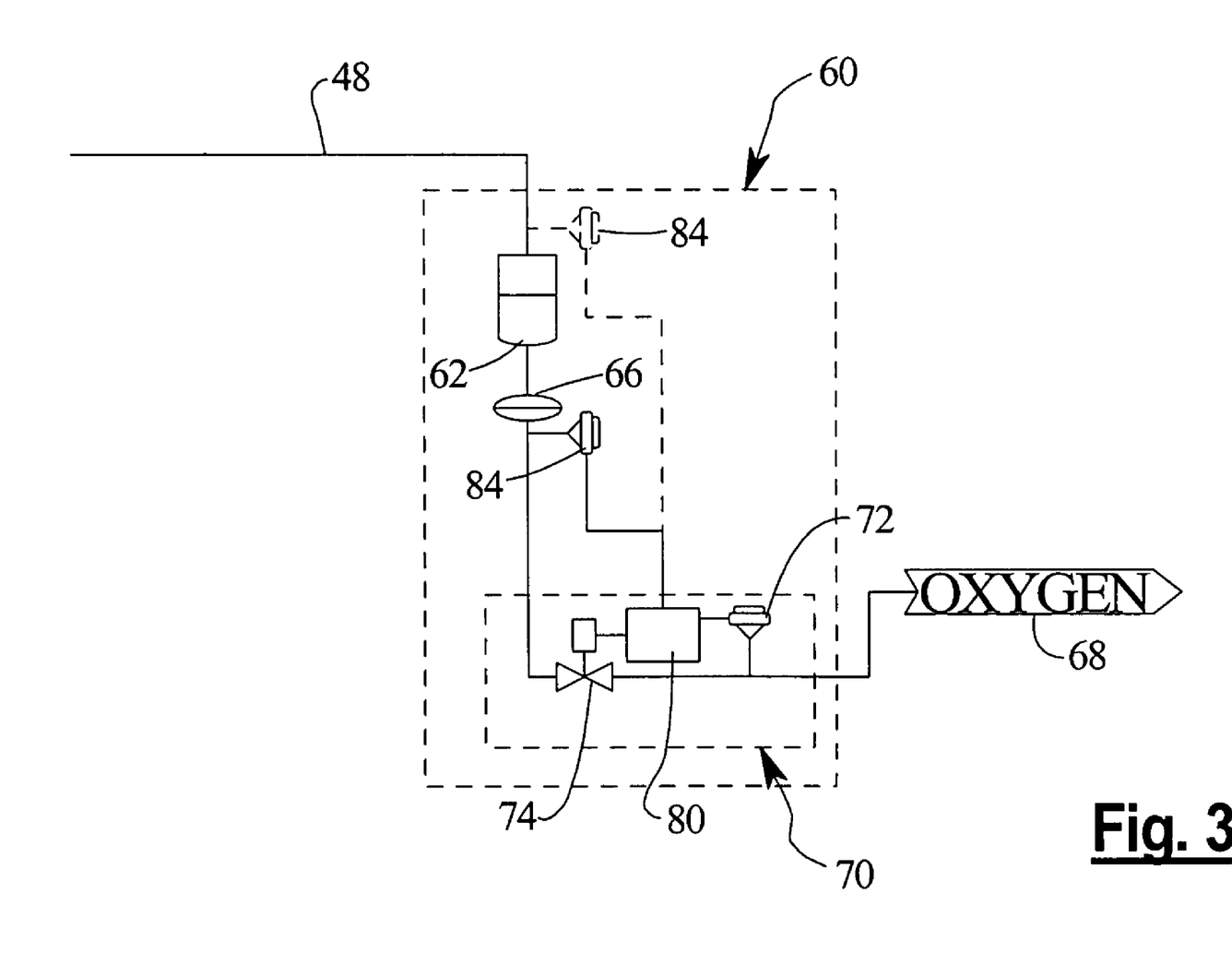
FIG. 3 is a schematic illustration of an alternate flow controller used in the invention.

Those PSA operating components may be as shown and configured to operate as described in U.S. Pat. No. 6,764,534. In an alternate embodiment as shown by FIG. 3, the operation may be as described in co-pending provisional application No. 60/617,833 entitled Oxygen Conserving Device with Variable Pulse Times and filed Oct. 12, 2004. In that embodiment, the apparatus as partially shown in FIG. 3 does not use a pressure regulator. As described in the above identified co-pending application, the desired volume of oxygen to be delivered on inhalation is determined by a sensing of the "volume" pressure by pressure transducer 84 at the mixing tank 62, which then when read by microprocessor 82 in conjunction with a reading of the operating cycle stage will access the look-up table for the selected flow setting and cause the flow control demand valve 74 to be opened for the time specified in the table.

Maximum breathing rates for the apparatus have been determined for the combination of each flow control switch setting and range of voltages that control the apparatus. Preferably, the apparatus is designed to operate in three settings of 1, 2 and 3 liters per minute (LPM) with an overall PSA cycle time of 11 seconds.

The concentration of the oxygen supplied by the apparatus for each setting of flow control switches 86 is dependent on system pressure, operating voltage (battery or external supply), and patient breathing rate within allowable ranges of these parameters. As in the embodiment shown in U.S. Pat. No. 6,764,534, the microprocessor calculates, from continuous or sampled readings of the selector position, the operating voltage, and the frequency of actuation of the flow controller 80, the predictable oxygen concentration being delivered to the user. If any of these approach the upper or lower thresholds, for example as low as 85% oxygen concentration, an intermittent alarm may be provided to warn the user that he or she can continue to use the apparatus but should take action to prevent the performance from falling outside of specifications. If any of the parameters regularly exceeds the predetermined thresholds, for example at a calculated oxygen concentration of 80% or less, the alarm may be programmed to sound continuously to notify the user that the performance of apparatus 20 is outside of specifications and its use discontinued.

For example, although the apparatus has been designed to accommodate reasonable breathing rates, a very significant increase in the physical activity of a user and the resulting increased breathing rate could cause the apparatus to be overdrawn by a demand of oxygen from the apparatus 20 more than it can supply. The embodiment shown preferably includes an audible signal at startup of the apparatus, both audible and a red visual light alarms to signal high and low pressure, system overdraw, and an apnea event (i.e., the absence of inhalation within a preset time), audible and yellow visual light alarms to signal a low battery condition, and a pulsing green light to indicate normal apparatus operation in a pulse mode.

The flow controller 80 continuously monitors the battery voltage, flow control switch setting, and the patient's breathing rate. If the breathing rate causes the apparatus to approach an overdraw condition (an oxygen concentration of about 85%) or to reach overdraw (a concentration of about 80% or less), the alarm either warns or alerts the patient to moderate his or her physical activity.

As in the embodiment shown in U.S. Pat. No. 6,764,534, the apparatus 20 may be powered by internal battery 98 or an external power supply that also can charge the internal battery. Also, the operating cycle may be controlled to function in the sequence and for the times disclosed as in U.S. Pat. No. 6,764,534 or other times suitable to the desired product gas output selections. Similarly, the circuitry, alarms and indicators may function in like manner. For example, in the embodiment described above and as shown in U.S. Pat. No. 6,764,534, the microprocessor monitors battery voltage, system pressure and flow rate; additional embodiments may include an oxygen monitoring system with the use of a blood oxygen sensor connectable to the user to measure the actual rather than the calculated concentration of oxygen being delivered to the user. In addition, those skilled in the art may be able to include other known safety features for use in monitored and/or unmonitored medical purposes.

It will be understood that various modifications and substitutions may be made to the described embodiment without departing from the spirit of the invention. Accordingly, the described preferred embodiment is intended for purposes of illustration and not as a limitation.

What is claimed is:

1. A gas delivery apparatus, comprising:
   a compressor for drawing ambient air into the apparatus;
   means for producing product gas having an increased concentration of oxygen relative to that of the ambient air;
   an apparatus outlet for delivering product gas to a user; and
   the producing means including:
      at least two adsorber beds, each bed including an inlet end for receiving ambient air and discharging adsorbed nitrogen as a waste gas and an outlet end for communicating and delivering the product gas to the apparatus outlet;
      first and second unitary manifolds on which the beds are directly mounted at their inlet ends and outlet ends, respectively, wherein the first manifold is configured to detachably mount the compressor, and wherein the first manifold includes a first internally formed channel for providing fluid communication of the bed inlet ends with the compressor and the second manifold includes an internally formed channel for providing fluid communication of the bed outlet ends with the apparatus outlet; and
      a unitary bolt centrally disposed between the beds and manifolds and engaging at least the second manifold and the compressor and passing through the first manifold to detachably retain and thereby support all of the beds, manifolds and compressor as an integrated operating unit.

2. The apparatus of claim 1 further comprising a mixing tank detachably mounted directly on the second manifold as part of the integrated operating unit and in fluid communication with the internally formed channel of the second manifold.

3. The apparatus of claim 1 further comprising a flow control valve actuated by inhalation by the user and detachably mounted directly on the second manifold as part of the integrated operating unit and in fluid connection with the internally formed channel of the second manifold.

4. The apparatus of claim 1 further comprising at least two inlet valves in fluid communication with the compressor and at least one of the bed inlets to control the flow of ambient air into the adsorber bed, the inlet valves being detachably mounted directly on the first manifold as part of the integrated operating unit.

5. The apparatus of claim 1 further comprising a second internally formed channel in the first manifold and at least two waste valves configured to control the flow of waste gases from the adsorber bed, the waste valves being detachably mounted directly on the first manifold as part of the operating unit and in fluid connection with the second internally formed channel.

6. A gas delivery apparatus, comprising:
   at least two adsorber beds for adsorbing nitrogen from ambient air and producing a product gas having an increased concentration of oxygen, each bed having an inlet end to receive the ambient air and discharge adsorbed nitrogen, and an outlet end for delivering at selectable times the product gas to an outlet of the apparatus;
   a first unitary manifold on which the beds are directly mounted at their inlet ends;
   a second unitary manifold on which the beds are directly mounted at their outlet ends;
   a compressor detachably mounted on the first manifold;
   at least one inlet channel integrally formed within the first unitary manifold and configured to be in fluid communication with at least one of the bed inlets and the compressor;
   at least one outlet channel integrally formed within the second unitary manifold and configured to be in fluid communication with at least one of the bed outlets and an outlet of the apparatus; and
   elongated bolt means centrally disposed between the beds and manifolds, and configured to detachably retain and thereby support the beds, manifolds and compressor as an integrated operating unit.

7. The apparatus according to claim 6, wherein the at least one outlet channel is further configured to be in fluid communication with a mixing tank detachably mounted directly on the second manifold as part of the integrated operating unit.

8. The apparatus according to claim 6, wherein the at least one outlet channel is further configured to be in fluid communication with a flow control valve detachably mounted to the second manifold as part of the integrated operating unit and the delivering at selectable times is determined by inhalation by the user.

9. The apparatus of claim 6, wherein the at least one outlet channel is further configured to be in fluid communication with at least one inlet valve detachably mounted directly on the first manifold as part of the integrated operating unit and wherein the at least one inlet valve is configured to control the flow of ambient air into at least one of the adsorber beds.

10. The apparatus according to claim 6, wherein the at least one inlet channel is further configured to communicate with at least one waste valve detachably mounted to the first manifold as part of the integrated operating unit and wherein the at least one waste valve is configured to control the flow of waste gases from at least one adsorber bed.

11. A gas delivery apparatus having at least two adsorber beds to adsorb nitrogen from ambient air to produce a product gas having an increased concentration of oxygen, each bed having an inlet end to receive the ambient air and discharge adsorbed nitrogen, and an outlet end for delivering at selectable times the product gas to an outlet of the apparatus, the improvement comprising:
a first unitary manifold on which the beds are directly mounted at their inlet ends;
a second unitary manifold on which the beds are directly mounted at their outlet ends;
means for detachably retaining the two beds and the manifolds together as an integrally removable unit with the beds supported by the manifolds and the detachable retaining means;
means for drawing ambient air into the apparatus;
means for discharging the adsorbed nitrogen from the apparatus;
an internal channel formed within the first manifold for providing fluid connection of the bed inlets with the drawing means and the discharging means; and
an internal channel formed within the second manifold for providing fluid connection of the bed outlets with the apparatus outlet.

12. The apparatus according to claim 11, in which the detachable retaining means is directly connected to at least one of the manifolds for holding the manifolds and beds together as an integrally removable unit.

13. The apparatus according to claim 11, in which the drawing means comprises a compressor to supply the ambient air under pressure to each of the adsorber beds, in which the compressor is detachably mounted directly on the first manifold as part of the integrally removable unit, and the compressor is in fluid communication with each of the adsorber bed inlets by the channel formed in the first manifold.

14. The apparatus according to claim 11 further comprising a mixing tank detachably mounted directly on the second manifold as part of the integrally removable unit, in which the mixing tank is in fluid communication with each of the adsorber bed outlets by the channel formed in the second manifold.

15. The apparatus according to claim 11 further comprising a flow control valve actuated by inhalation by the user to deliver product gas to the user, in which the flow control valve is detachably mounted directly on the second manifold as part of the integrally removable unit, and the flow control valve is in fluid communication with each of the adsorber bed outlets and the mixing tank by the channel formed in the second manifold.

16. The apparatus according to claim 15, in which the detachable retaining means is directly connected to at least one of the manifolds for holding the manifolds, flow control valve and beds together as an integrally removable unit.

17. The apparatus according to claim 15, and further comprising at least two inlet valves, each of which is in fluid connection between the ambient air drawing means and one of the bed inlets to control the flow of ambient air into the adsorber bed, in which the inlet valves are detachably mounted directly on the first manifold as part of the integrally removable unit, and the inlet valves are in fluid communication with their respective adsorber bed inlets by the channel formed in the first manifold.

18. The apparatus according to claim 17, in which the detachable retaining means is directly connected to at least one of the manifolds for holding the manifolds, flow control valve, inlet valves and beds together as an integrally removable unit.

19. The apparatus according to claim 15, and further comprising at least two waste valves, each of which is in fluid connection between the discharging means and one of the bed inlets to control the flow of waste gases from the adsorber bed, in which the waste valves are detachably mounted directly on the first manifold as part of the integrally removable unit, and the waste valves are in fluid communication with their respective adsorber bed inlets by the channel formed in the first manifold.

20. The apparatus according to claim 19, in which the detachable retaining means is directly connected to at least one of the manifolds for holding the manifolds, flow control valve, waste valves and beds together as an integrally removable unit.

* * * * *